US012754189B2

(12) United States Patent
Tanaka et al.

(10) Patent No.: US 12,754,189 B2
(45) Date of Patent: Oct. 6, 2026

(54) DRUG-SPECIFIC PHARMACOKINETIC ASSAY FOR IL-15 SUPERAGONIST

(71) Applicant: NANTCELL, INC., Culver City, CA (US)

(72) Inventors: Shiho Tanaka, Culver City, CA (US); Kayvan Niazi, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 927 days.

(21) Appl. No.: 18/006,668

(22) PCT Filed: Jul. 21, 2021

(86) PCT No.: PCT/US2021/042531
§ 371 (c)(1),
(2) Date: Jan. 24, 2023

(87) PCT Pub. No.: WO2022/031440
PCT Pub. Date: Feb. 10, 2022

(65) Prior Publication Data

US 2023/0280356 A1 Sep. 7, 2023

Related U.S. Application Data

(60) Provisional application No. 63/060,256, filed on Aug. 3, 2020.

(51) Int. Cl.

| | |
|---|---|
| ***G01N 33/68*** | (2006.01) |
| ***C07K 14/54*** | (2006.01) |
| ***C07K 14/715*** | (2006.01) |

(52) U.S. Cl.
CPC ..... *G01N 33/6869* (2013.01); *C07K 14/5443* (2013.01); *C07K 14/7155* (2013.01); *C07K 2319/30* (2013.01); *G01N 2333/5443* (2013.01); *G01N 2333/7155* (2013.01)

(58) Field of Classification Search
None
See application file for complete search history.

(56) References Cited

U.S. PATENT DOCUMENTS 5,582,996 A 12/1996 Curtis

FOREIGN PATENT DOCUMENTS

| | | | |
|---|---|---|---|
| WO | WO 02/04952 | 1/2002 | |
| WO | WO 2009/062520 | 5/2009 | |
| WO | WO 2011/031986 | 3/2011 | |
| WO | WO-2012040323 A2 * | 3/2012 | .............. A61P 31/18 |
| WO | WO 2017/067672 | 4/2017 | |
| WO | WO 2017/196867 | 11/2017 | |
| WO | WO 2018/075989 | 4/2018 | |
| WO | WO 2019/246379 | 12/2019 | |

OTHER PUBLICATIONS

Han et al (Cytokine. Dec. 2011 ; 56(3): 804-810) (Year: 2011).*
Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Lazar et al. (Mol. Cell. Biol., 8:1247-1252, 1988) (Year: 1988).*
Bork (Genome Research, 2000, 10:398-400) (Year: 2000).*
Kulmanov et al (Bioinformatics, 34(4), 2018, 660-668) (Year: 2018).*
Vajdos et al. (J Mol Biol. Jul. 5, 2002;320(2):415-28) (Year: 2002).*
Brown et al. (J Immunol. May 1996;156(9):3285-91) (Year: 1996).*
Vattekatte, (PeerJ. Mar. 6, 2020:8:e8408. doi: 10.7717/peerj.8408. eCollection 2020.) (Year: 2020).*
Edwards et al. (Mol Biol. Nov. 14, 2003;334(1):103-18) (Year: 2003).*
Lloyd et al. (Protein Eng Des Sel. Mar. 2009;22(3):159-68. Epub Oct. 29, 2008.) (Year: 2009).*
Goel et al. (J Immunol. Dec. 1, 20045;173(12):7358-67) (Year: 2004).*
Khan et al. (J Immunol (2014) 192 (11): 5398-5405) (Year: 2014).*
Poosarla et al. (Biotechnol Bioeng. Jun. 2017 ; 114(6): 1331-1342) (Year: 2017).*
Rabia, et al. (Biochem Eng J. Sep. 15, 2018:137:365-374. Epub Jun. 5, 2018) (Year: 2018).*
Alter et al., "Targeted IL-15-based Protein Fusion Complexes as Cancer Immunotherapy Approaches," Journal of Immunological Sciences, 2018, vol. 2(1), pp. 15-18.
Liu et al., "A Novel Fusion of ALT-803 (Interleukin (IL)-15 Superagonist) with an Antibody Demonstrates Antigen-specific Antitumor Responses," Journal of Biological Chemistry, Nov. 11, 2016, vol. 291(46), pp. 23869-23881.
Official Action for Australian Patent Application No. 2024203099, dated May 29, 2025 4 pages.
Notice of Allowance for Australian Patent Application No. 2024203099, dated Jun. 17, 2025 3 pages.
Notice of Allowance for Korean Patent Application No. 10-2023-7007631, dated Jun. 26, 2025 14 pages.
Official Action for Australian Patent Application No. 2021320085, dated Apr. 4, 2024 4 pages.
International Preliminary Report on Patentability for International (PCT) Patent Application PCT/US2021/042531, dated Feb. 16, 2023 7 pages.
Han et al., "IL-15:IL-15 receptor alpha superagonist complex: High-level co-expression in recombinant mammalian cells, purification and characterization," Cytokine, author manuscript, 18 pages, Dec. 2011, vol. 56(3), pp. 804-810.
Liu et al., "Evaluation of the biological activities of he IL-15 superagonist complex, ALT-803, following intravenous versus subcutaneous administration in murine models," Cytokine, author manuscript, 21 pages, Jul. 1, 2018, vol. 107, pp. 105-112.
International Search Report and Written Opinion for International (PCT) Patent Application PCT/US2021/042531, dated Oct. 29, 2021 10 pages.

* cited by examiner

*Primary Examiner* — Brian Gangle
*Assistant Examiner* — Andrea K McCollum
(74) *Attorney, Agent, or Firm* — Sheridan Ross P.C.

(57) ABSTRACT

Provided herein, are methods and compositions for detecting heteromeric protein complexes in biological samples. The methods and compositions allow for capturing and detecting the protein complex with substantially the same antibody, while avoiding detection of native proteins.

14 Claims, 9 Drawing Sheets

Specification includes a Sequence Listing.

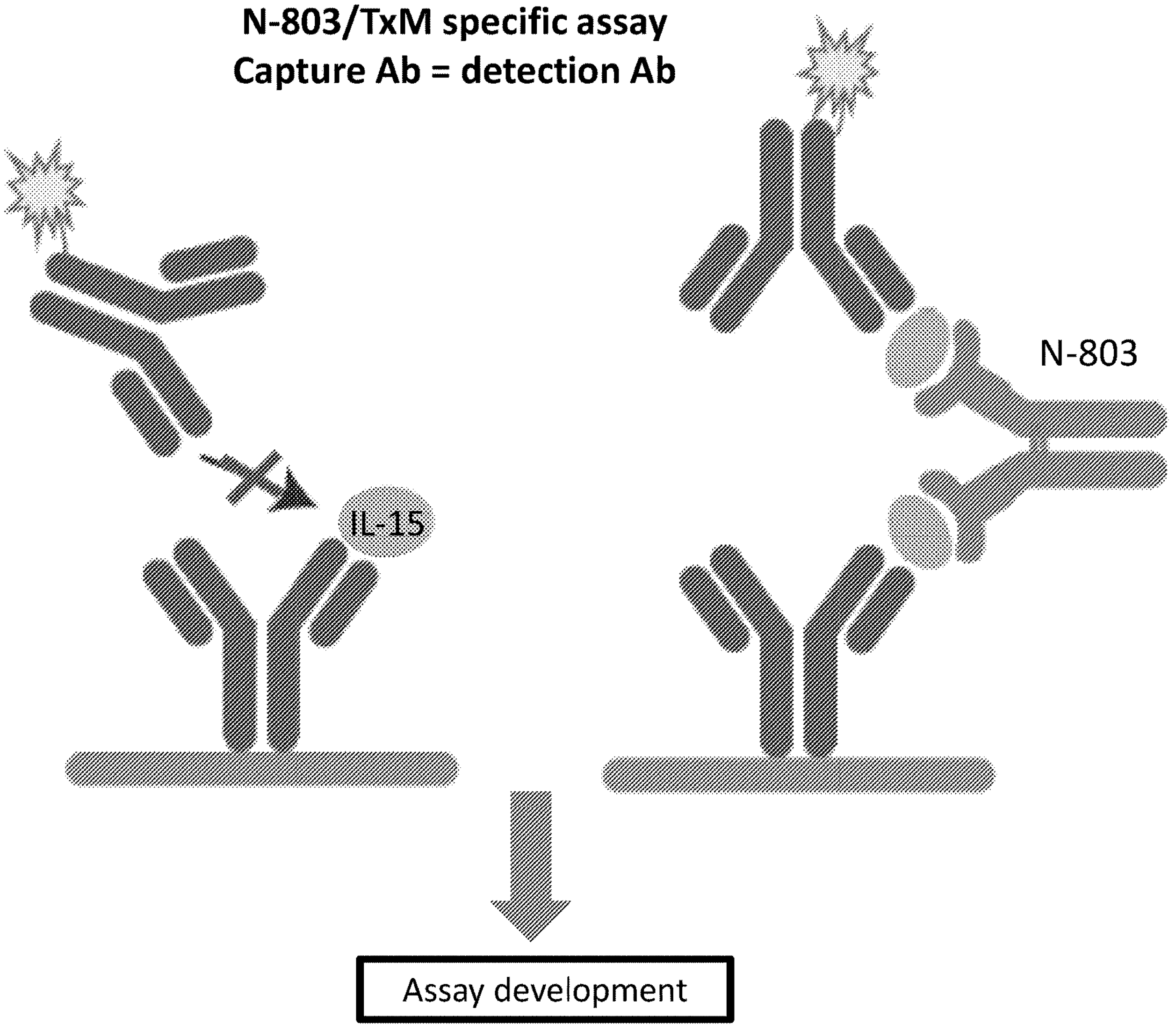
FIG. 1B - continued

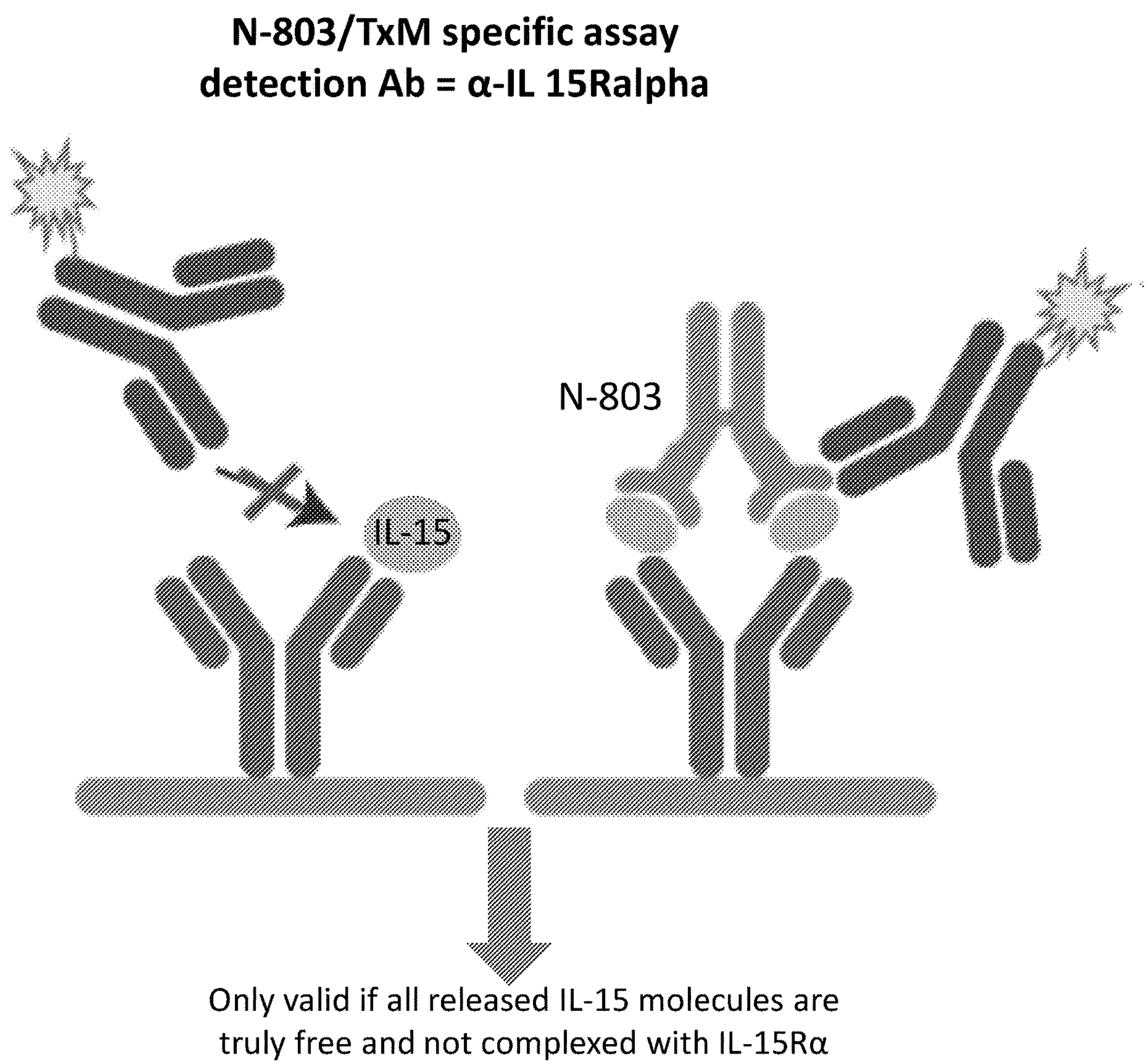
FIG. 1B - continued

SEQUENCE LISTING

```
<160> NUMBER OF SEQ ID NOS: 1

<210> SEQ ID NO 1
<211> LENGTH: 65
<212> TYPE: PRT
<213> ORGANISM: Homo sapiens

<400> SEQUENCE: 1

Ile Thr Cys Pro Pro Pro Met Ser Val Glu His Ala Asp Ile Trp Val
```

-continued

```
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65
```

DRUG-SPECIFIC PHARMACOKINETIC ASSAY FOR IL-15 SUPERAGONIST

CROSS-REFERENCE TO RELATED APPLICATIONS

This application is a national stage application under 35 U.S.C. 371 and claims the benefit of PCT Application No. PCT/US2021/042531 having an international filing date of 21 Jul. 2021, which designated the United States, and which PCT application claims the benefit of priority under 35 U.S.C. § 119 (e) to U.S. Provisional Application Ser. No. 63/060,256, filed 3 Aug. 2020. The entire disclosures of each of U.S. Provisional Application Ser. No. 63/060,256 and PCT Application No. PCT/US2021/042531 are incorporated herein by reference.

REFERENCE TO A SEQUENCE LISTING

This application contains a Sequence Listing submitted electronically as a text file by EFS-Web. The text file, named "054692-645P01US_SEQUENCE_LISTING.TXT", has a size in bytes of 1000 bytes, and was recorded on Jul. 8, 2020. The information contained in the text file is incorporated herein by reference in its entirety pursuant to 37 CFR § 1.52(e)(5).

BACKGROUND

Therapeutic heteromer protein complexes, including the interleukin-15 (IL-15) superagonist N-803, have been found to modulate the immune response for treatment of various cancers. N-803 is a multimeric protein complex including an IL-15 mutant bound to an IL-15 receptor α, which is in turn attached to an immunoglobulin G1 (IgG1) crystallizable fragment (Fc). N-803 has been shown to display improved pharmacokinetic properties, longer persistence in lymphoid tissues and enhanced anti-tumor activity compared to native, non-complexed IL-15.

Continued evaluation of pharmacokinetic properties of therapeutic heteromer protein complexes such as N-803 is critical for assessing clinical efficacy. Currently available pharmacokinetic assays do not distinguish between N-803 and native IL-15, and may potentially measure IL-15 levels in patient serum in addition to the target N-803. Thus, methods for specific detection of therapeutic heteromer protein complexes are needed. Provided herein, inter alia, are solutions to these and other problems in the art.

SUMMARY

One embodiment relates to a composition including: (a) a first interleukin 15 receptor alpha Sushi domain (IL-15RαSu); (b) a second IL-15RαSu domain, wherein the first and second IL-15RαSu domains are covalently joined by a disulfide bond; (c) a first IL-15 domain, bound by electrostatic interactions to the first IL-15RαSu domain to form a first IL-15/IL-15RαSu complex; (d) a second IL-15 domain, bound by electrostatic interactions to the second IL-15RαSu domain to form a second IL-15/IL-15RαSu complex; (e) a first monoclonal antibody (mAb) bound to an epitope on the first IL-15/IL-15RαSu complex; and (f) a second mAb bound to the identical epitope on the second IL-15/IL-15RαSu complex, wherein both the first mAb and the second mAb bind to the epitopes with equal affinity.

Another embodiment relates to a method for detecting a heterotetrameric IL-15/IL-15RαSu complex in a biological sample is provided, the method including: a) contacting the biological sample including the protein complex with a first mAb, wherein the mAb is conjugated to a polymeric surface, wherein the heterotetrameric complex includes two IL-15 domains and two IL-15RαSu, wherein each IL-15 domain is electrostatically bound to an IL-15RαSu domain, wherein the two IL-15RαSu domains are covalently bound to each other by a disulfide bond, and wherein the Fab portion of the mAb binds an epitope on the IL-15/IL-15RαSu complex with an affinity between 500 nM and 1 IM; b) contacting the biological sample with a second mAb under conditions such that the second antibody binds with the same affinity to the identical epitope on the second IL-15/IL-15RαSu complex; c) washing unbound complexes from the polymeric surface; and detecting binding of the second mAb.

In one aspect of any of the embodiments, at least one of the IL-15 domains comprises an asparagine-to-aspartate mutation at amino acid position 72 (N72D).

In one aspect of any of the embodiments, the IL-15RαSu domains each further comprise an immunoglobulin crystallizable fragment (Fc) domain. In another aspect, the IL-15RαSu domains further comprise an scFv domain.

In one aspect of any of the embodiments, the first mAb is conjugated to a polymeric surface.

In one aspect of any of the embodiments, the second mAb comprises a detection means. In one aspect, the detection means is selected from the group consisting of a fluorophore, a radioisotope, and an enzyme.

In one aspect of any of the embodiments, the IL-15 domains further comprise a single chain variable fragment (scFv) domain.

In one aspect of any of the embodiments, the polymeric surface is a polypropylene or polystyrene surface.

In one aspect of any of the embodiments, the first mAb and the second mAb have substantially the same amino acid sequence.

DETAILED DESCRIPTION

Figure 1A:
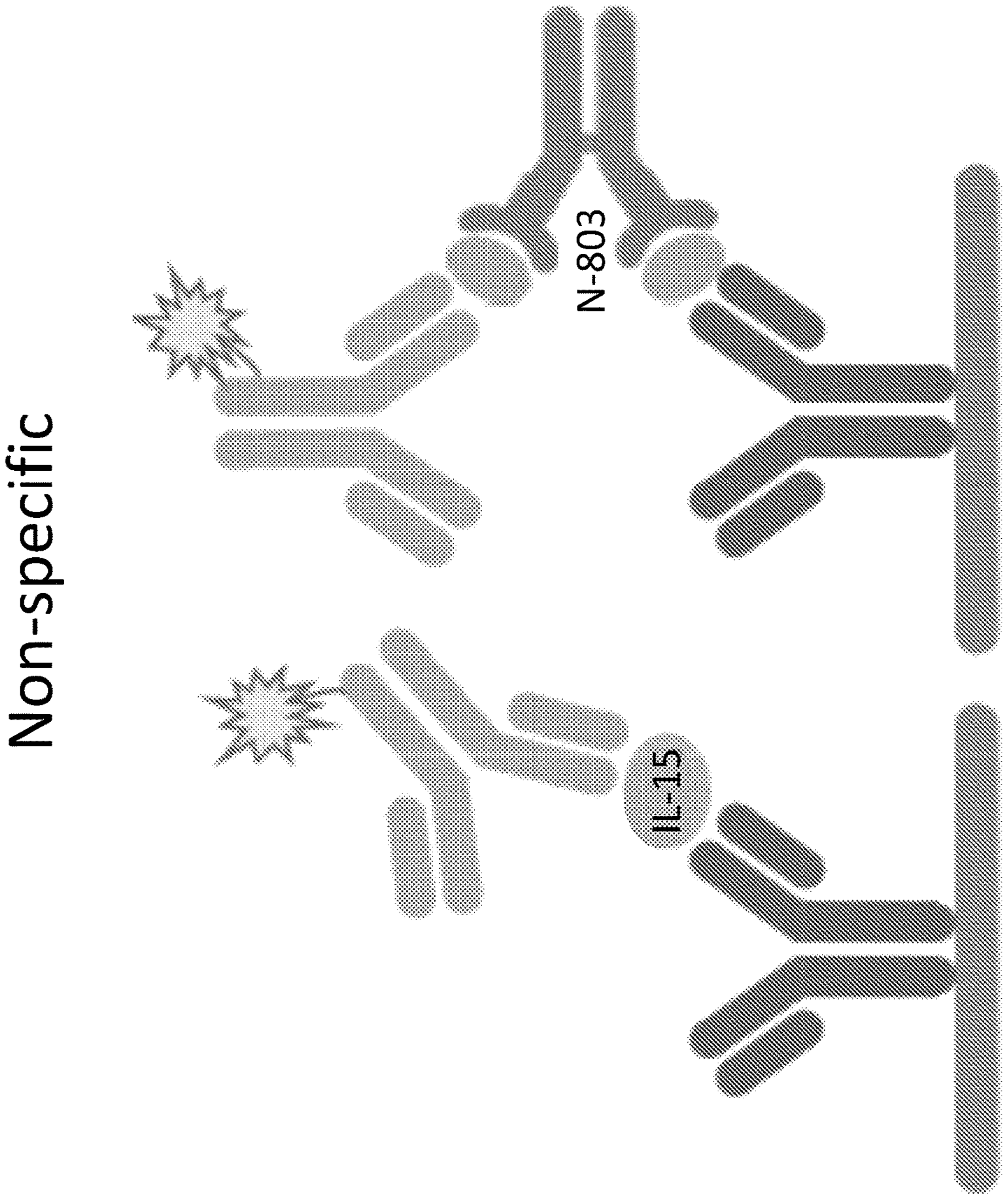
FIG. 1A is a schematic of a pharmacokinetic assay for detecting a heteromeric protein complex, where two different antibodies are used, one for capture and one for detection.

After reading this description it will become apparent to one skilled in the art how to implement the present disclosure in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present disclosure as set forth herein.

Before the present technology is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description divided into various sections only for the reader's convenience and disclosure found in any section may be combined with that in another section. Titles or subtitles may be used in the specification for the convenience of a reader, which are not intended to influence the scope of the present disclosure.

Definitions

Unless defined otherwise, all technical and scientific terms used herein have the same meaning as commonly understood by one of ordinary skill in the art to which this disclosure belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

As used herein, the terms "Fc domain" or "fragment crystallizable domain" are used in accordance with their plain and ordinary meanings and refer to any of the recombinant or naturally-occurring forms of the "base" or tail-end region (C-terminal) of an antibody. The Fc domain is typically composed of two heavy chains that contribute two or three constant domains depending on the class of the antibody. The Fc region is comprised of two heavy chain constant Ig domains in the antibodies IgG, IgA, and IgD, and of three heavy chain constant Ig domains in the antibodies IgE and IgM.

The term "Fc" refers to a non-antigen-binding fragment of an antibody. Such an "Fc" can be in monomeric or multimeric form. The original immunoglobulin source of the native Fc is preferably of human origin and may be any of the immunoglobulins. In embodiments, the Fc is an IgG1 or IgG2 Fc. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term “Fc” as used herein is generic to the monomeric, dimeric, and multimeric forms.

In embodiments, the term “Fc” refers to a molecule or sequence that is modified from a native Fc, but still comprises a binding site for a receptor. As with modified Fc and native Fc’s, the term “Fc domain” includes molecules in monomeric or multimeric form, whether digested from whole antibody or produced by recombinant gene expression or by other means.

In embodiments, the Fc is attached, either directly or indirectly, to an IL-15Rα or an IL-15 domain. In embodiments, the Fc is covalently and/or genetically fused with an IL-15Rα or an IL-15 domain.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

The phrase “specifically (or selectively) binds” to an antibody or “specifically (or selectively) immunoreactive with,” when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A “chimeric antibody” is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A “protein complex” or “complex” as used herein refers to two or more polypeptides that associate simultaneously. The complexes may be constructed through binding between proteins and/or binding between receptors and ligands. The proteins may be associated through non-covalent protein-protein interactions, though certain polypeptides in the complex may also be covalently linked directly or indirectly through, for example, a chemical linker, a bond or another protein. For example, the heterotetrameric IL-15/IL-15RαSu complex includes two IL-15 domains non-covalently bound to two IL-15RαSu domains, wherein the two IL-15RαSu domains are attached covalently by a disulfide bond.

A “detectable means” or “detectable moiety” is a composition, substance, element, or compound; or moiety thereof; detectable by appropriate means such as spectroscopic, photochemical, biochemical, immunochemical, chemical, magnetic resonance imaging, or other physical means.

For example, a detectable means includes $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$. $^{89}Sr$, $^{89}Zr$, $^{94}Tc$, $^{94}Tc$, $^{99m}Tc$, $^{99}Mo$, $^{105}Pd$, $^{105}Rb$, $^{111}Ag$, $^{111}In$, $^{123}I$, $^{124}I$, $^{125}I$, $^{131}I$, $^{142}Pr$, $^{143}Pr$, $^{149}$ Pm, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide (“USPIO”) nanoparticles, USPIO nanoparticle aggregates, superparamagnetic iron oxide (“SPIO”) nanoparticles, SPIO nanoparticle aggregates, monochrystalline iron oxide nanoparticles, monochrystalline iron oxide, nanoparticle contrast agents, liposomes or other delivery vehicles containing Gadolinium chelate (“Gd-chelate”) molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable means may be a monovalent detectable agent or a detectable agent capable of forming a bond with another composition.

As used herein, the term "conjugate" refers to the association between atoms or molecules. The association can be direct or indirect. For example, a conjugate between an antigen binding domain and a peptide compound can be direct, e.g., by covalent bond (e.g., a disulfide bond), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be an antibody and a fusion protein, biological sample, etc. as described herein.

A "control" sample or value refers to a sample that serves as a reference, usually a known reference, for comparison to a test sample. For example, a test sample can be taken from a test condition (e.g., in the presence of a test compound), and compared to samples from known conditions (e.g., in the absence of the test compound (negative control), or in the presence of a known compound (positive control)). A control can also represent an average value gathered from a number of tests or results. One of skill in the art will recognize that controls can be designed for assessment of any number of parameters. For example, a control can be devised to determine a background level of signal (negative control) or an expected level of signal (e.g., a standard curve or positive control). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

The term "polymeric" refers to a molecule including repeating subunits (e.g., polymerized monomers). For example, polymeric molecules may be based upon polypropylene (PP), polystyrene (PS), polyethylene glycol (PEG), poly [amino(1-oxo-1,6-hexanediyl)], poly(oxy-1,2-ethanediyloxycarbonyl-1,4-phenylenecarbonyl), tetraethylene glycol (TEG), polyvinylpyrrolidone (PVP), poly(xylene), or poly(p-xylylene). See, for example, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA, which are incorporated by reference in their entirety for all purposes.

An "interleukin-15 protein" or "IL-15" as referred to herein includes any of the recombinant or naturally-occurring forms of the interleukin-15 (IL-15) protein or variants or homologs thereof that maintain IL-15 protein activity (e.g. within at least 50%, 80%, 90%, 95%, 96%, 97%, 98%, 99% or 100% activity compared to IL-15 protein). In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-15 protein. In embodiments, the IL-15 protein is substantially identical to the protein identified by the UniProt reference number P40933 or a variant or homolog having substantial identity thereto.

An "interleukin-15 receptor subunit alpha protein" or "IL-15Rα" as referred to herein includes any of the recombinant or naturally-occurring forms of the interleukin-15 receptor subunit alpha (IL-15Rα) protein or variants or homologs thereof that maintain IL-15Rα protein activity (e.g. within at least 50%, 80%, 90%, 95%, 96%, 97%, 98%, 99% or 100% activity compared to IL-15Rα protein). In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-15Rα protein. In embodiments, the IL-15Rα protein is substantially identical to the protein identified by the UniProt reference number Q13261 or a variant or homolog having substantial identity thereto.

As used herein, "domain" refers to a conserved portion of a protein that functions and exists independently of the rest of the protein sequence. A domain may form a stable, three-dimensional structure that exists as a functional unit independent of the remaining protein. For example, the IL-15RαSu domain is the portion of IL-15Rα that retains the IL-15 binding activity.

As used herein, "IL-15 domain" refers to a polypeptide comprising at least a portion of a sequence of the IL-15 protein. In embodiments, the IL-15 domain comprises at least a portion of the sequence of the IL-15 protein and includes one or more amino acid substitutions or deletions within the amino acid sequence of the IL-15 protein. In embodiments, the IL-15 domain is an IL-15 variant that comprises a different a different amino acid sequence compared to the IL-15 protein. In embodiments, the IL-15 domain binds the IL-15Rα protein or a fragment thereof. In embodiments, the IL-15 domain is bound to the IL-15Rα, protein or a fragment thereof in embodiments, the sequence of the IL-15 domain has at least one amino acid change, e.g. substitution or deletion, compared to the IL-15 protein. In embodiments, the amino acid substitutions/deletions are in the portions of IL-15 that interact with IL-15Rβ and/or γC. In embodiments, the amino acid substitutions/deletions do not affect binding to the IL-15Rα polypeptide or the ability to produce the IL-15 domain. In embodiments, amino acid substitutions can be conservative or non-conservative changes and insertions of additional amino acids compared to the IL-15 protein. In embodiments, the IL-15 domain comprises one or more than one amino acid substitutions/deletions at position 6, 8, 10, 61, 65, 72, 92, 101, 104, 105, 108, 109, 111, or 112 of the IL-15 protein sequence. In embodiments, the IL-15 domain comprises an N72D substitution of the IL-15 protein sequence.

The term "sushi domain" as used herein refers to a common motif in proteins comprising a beta-sandwich arrangement. Sushi domains are common in protein-protein interactions, and typically include four cysteines forming two disulfide bonds in a 1-3 and 2-4 pattern. For example, the region of IL-15Rα that binds IL-15 includes a sushi domain.

In embodiments, the IL-15Rα sushi domain includes the amino acid sequence comprising the sequence of SEQ ID NO:1. In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to the sequence of SEQ ID NO:1. In embodiments, the IL-15Rα sushi domain associates with the IL-15 protein. In embodiments, the IL-15Rα sushi domain associates with the IL-15 domain.

Compositions and Methods

In an aspect is provided a composition including: (a) a first interleukin 15 receptor alpha Sushi domain (IL-15RαSu); (b) a second IL-15RαSu domain, wherein the first and second IL-15RαSu domains are covalently joined by a disulfide bond; (c) a first IL-15 domain, bound by electrostatic interactions to the first IL-15RαSu domain to form a first IL-15/IL-15RαSu complex; (d) a second IL-15 domain, bound by electrostatic interactions to the second IL-15RαSu domain to form a second IL-15/IL-15RαSu complex; (e) a first monoclonal antibody (mAb) bound to an epitope on the first IL-15/IL-15RαSu complex; and (f) a second mAb bound to an identical epitope on the second IL-15/IL-15RαSu complex, wherein both the first mAb and the second mAb bind to the epitopes with equal affinity.

In embodiments, at least one of the IL-15 domains includes an asparagine-to-aspartate mutation at amino acid position 72 (N72D). In embodiments, the IL-15RαSu domains each further include an immunoglobulin crystalizable fragment (Fc) domain. In embodiments, the first mAb is conjugated to a polymeric surface.

In embodiments, the second mAb includes a detection means. In embodiments, the detection means is selected from the group consisting of a fluorophore, a radioisotope, and an enzyme. In embodiments, the detection means is a fluorophore. In embodiments, the detection means is a radioisotope. In embodiments, the detection means is an enzyme.

In embodiments, the IL-15 domains further include a single chain variable fragment (scFv) domain.

In an aspect is provided a method for detecting a heterotetrameric IL-15/IL-15RαSu complex in a biological sample, the method including: a) contacting the biological sample including the protein complex with a first mAb, wherein the mAb is conjugated to a polymeric surface, wherein the heterotetrameric complex comprises two IL-15 domains and two IL-15RαSu, wherein each IL-15 domain is electrostatically bound to an IL-15RαSu domain, wherein the two IL-15RαSu domains are covalently bound to each other by a disulfide bond, and wherein the Fab portion of the mAb binds an epitope on the IL-15/IL-15RαSu complex with an affinity between 500 nM and 1 fM; b) contacting the biological sample with a second mAb under conditions such that the second antibody binds with the same affinity to the identical epitope on the second IL-15/IL-15RαSu complex; c) washing unbound complexes from the polymeric surface; and d) detecting binding of the second mAb.

In embodiments, at least one of the IL-15 domains includes an N72D mutation. In embodiments, both IL-15 domains include an N72D mutation. In embodiments, the IL-15RαSu domains each further include an Fc domain.

In embodiments, the second mAb includes a detection means. In embodiments, the detection means is selected from the group consisting of a fluorophore, a radioisotope, and an enzyme. In embodiments, the detection means is a fluorophore. In embodiments, the detection means is a radioisotope. In embodiments, the detection means is an enzyme.

In embodiments, the polymeric surface is a polypropylene or polystyrene surface. In embodiments, the polymeric surface is a polypropylene surface. In embodiments, the polymeric surface is a polystyrene surface.

In embodiments, the first mAb and the second mAb have substantially the same amino acid sequence.

In embodiments, the IL-15 domains each further comprise an scFv domain. In embodiments, the IL-15RαSu domains each further comprise an scFv domain.

In embodiments, the heterotetrameric IL-15/IL-15RαSu complex is a fusion protein as described in WO 2008/143794, WO 2012/040323, WO 2016/004060, and WO 2017/053649, each of which is incorporated herein by reference in its entirety. In embodiments, the heterotetrameric IL-15/IL-15RαSu complex is N-803 (also referred to as ALT-803 or NANT-803). In embodiments, the complex is TxM. In embodiments, the complex is N-820.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

One skilled in the art would understand that descriptions of making and using the particles described herein is for the sole purpose of illustration, and that the present disclosure is not limited by this illustration.

Example 1. Pharmacokinetic Assay Development

The compositions and methods described herein including embodiments thereof allow for specific detection of heteromeric therapeutic protein complexes, including superagonist complexes N-803, TxM, and N-820.

Currently available assays are not capable of specifically detecting therapeutic protein complexes that include IL-15, and thus are unsuitable for assessing pharmacokinetic properties of the therapeutics in preclinical and clinical studies. As shown in FIG. 1A, existing detection systems that employ capture and detection antibodies that recognize different epitopes of IL-15 bind non-specifically to both endogenous IL-15 and N-803. This results in erroneously higher measurements of N-803 concentration. Thus, various other approaches were tested for specific quantification and detection of various heteromeric protein complexes, as illustrated in the schematic of FIG. 1B.

First, an assay was tested where different antibodies were used for capture and detection of the N-803 heteromeric protein. An anti-IL-15 antibody was used for capture and an anti-human IgG Fc antibody for used for detection (FIG. 1B, left panel). However, serum antibodies interfered with detection of the N-803 Fc domain, thus rendering this method unsuccessful. Another method was tested wherein an anti-IL-15 antibody and an anti-IL-15Rα antibody were used for capture and detection, respectively (FIG. 1B, right panel). However, results indicated that this method is only accurate if all native IL-15 in the sample is unbound and not complexed with IL-15Rα, which would result in non-specific detection of protein complexes.

Figure 1B:
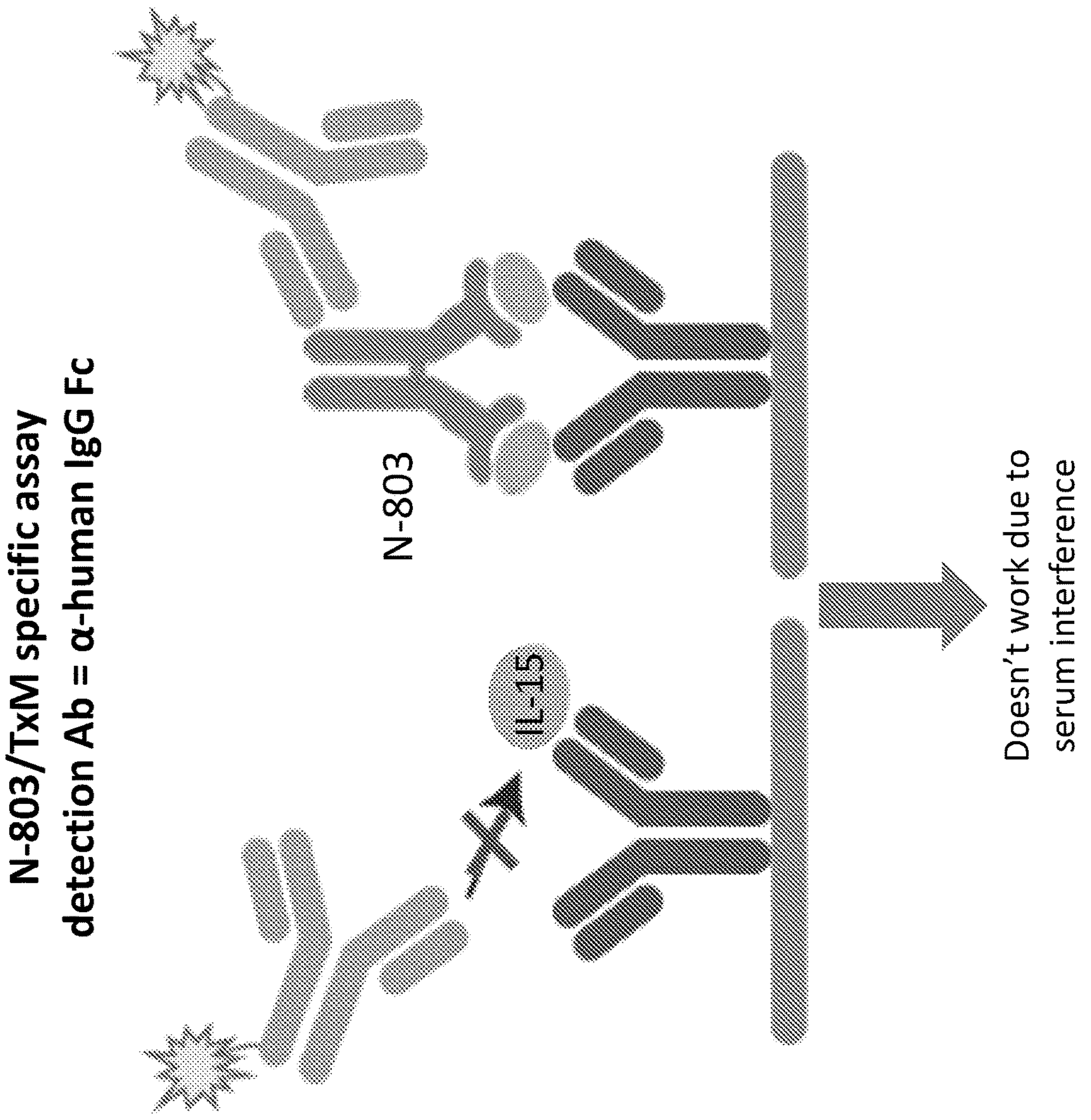
FIG. 1B are schematics illustrating three approaches for detecting therapeutic protein complexes that include IL15Rα and IL-15. The schematics show assay designs where an anti-IL-15 antibody is used to capture the protein complex. For detection of the complex, an anti-human IgG Fc detection antibody (left panel), an anti-IL-15 antibody substantially similar to the capture antibody (center panel), or an anti-IL15Rα antibody (right panel) was used.
Figure 2:
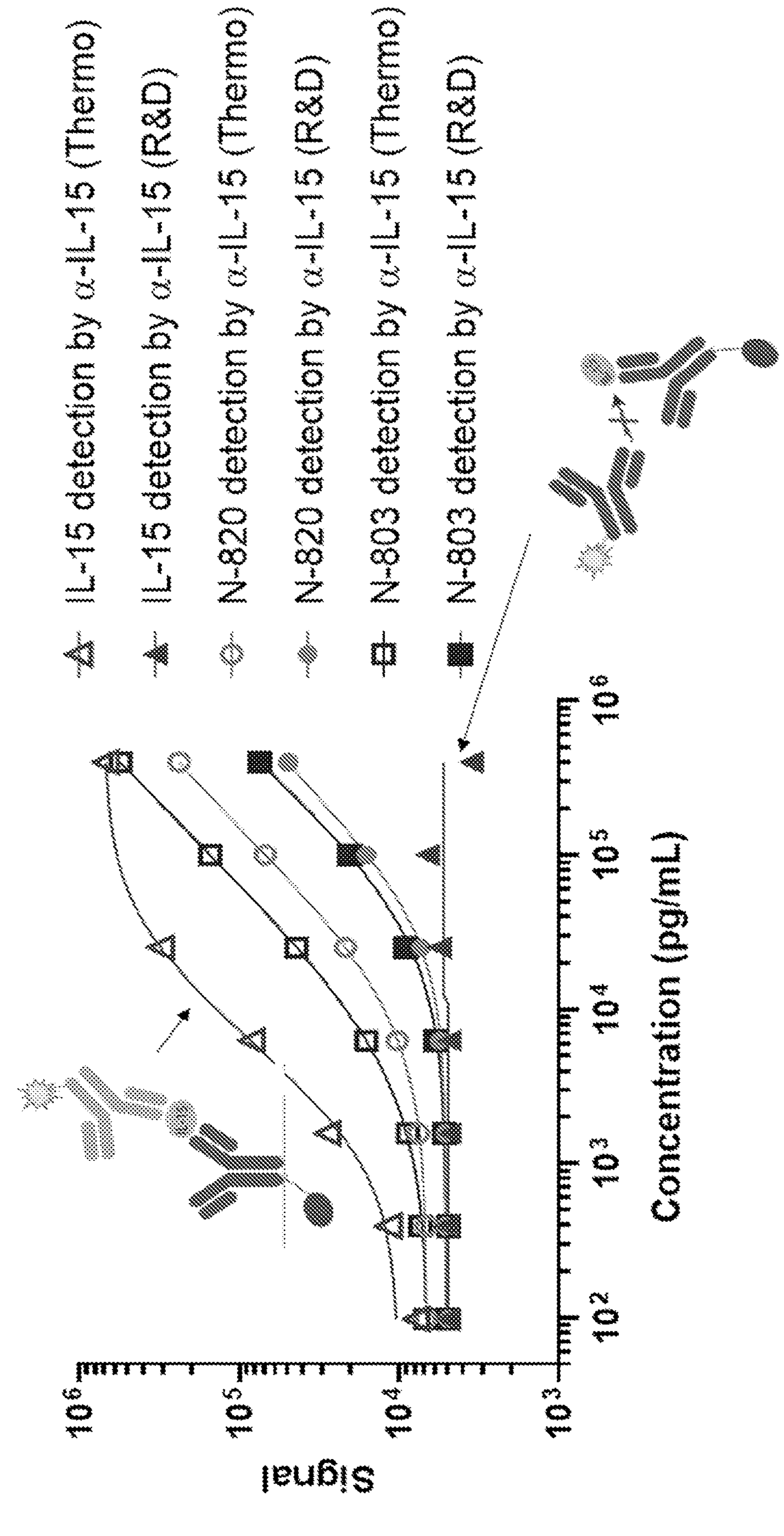
FIG. 2 is a graph showing that substantially identical monoclonal anti-IL-15 antibodies used for both capture and detection specifically detect the heteromer protein complex.

An approach where the same monoclonal anti-IL-15 antibody was employed for both capture and detection was tested (FIG. 1B, middle panel). Once the monoclonal anti-IL-15 antibody bound to an IL-15 molecule, the same IL-15 molecule could not be recognized by a second antibody, for example the capture antibody, since the epitope is already bound. Since N-803 comprises two IL-15 molecules, a second anti-IL-15 antibody was able to bind the second IL-15 of the N-803 heteromeric protein complex. This allows for binding of both the capture and detection antibody to a single N-803 protein complex, without non-specific detection of native IL-15, as illustrated by FIG. 2.

Figure 3A:
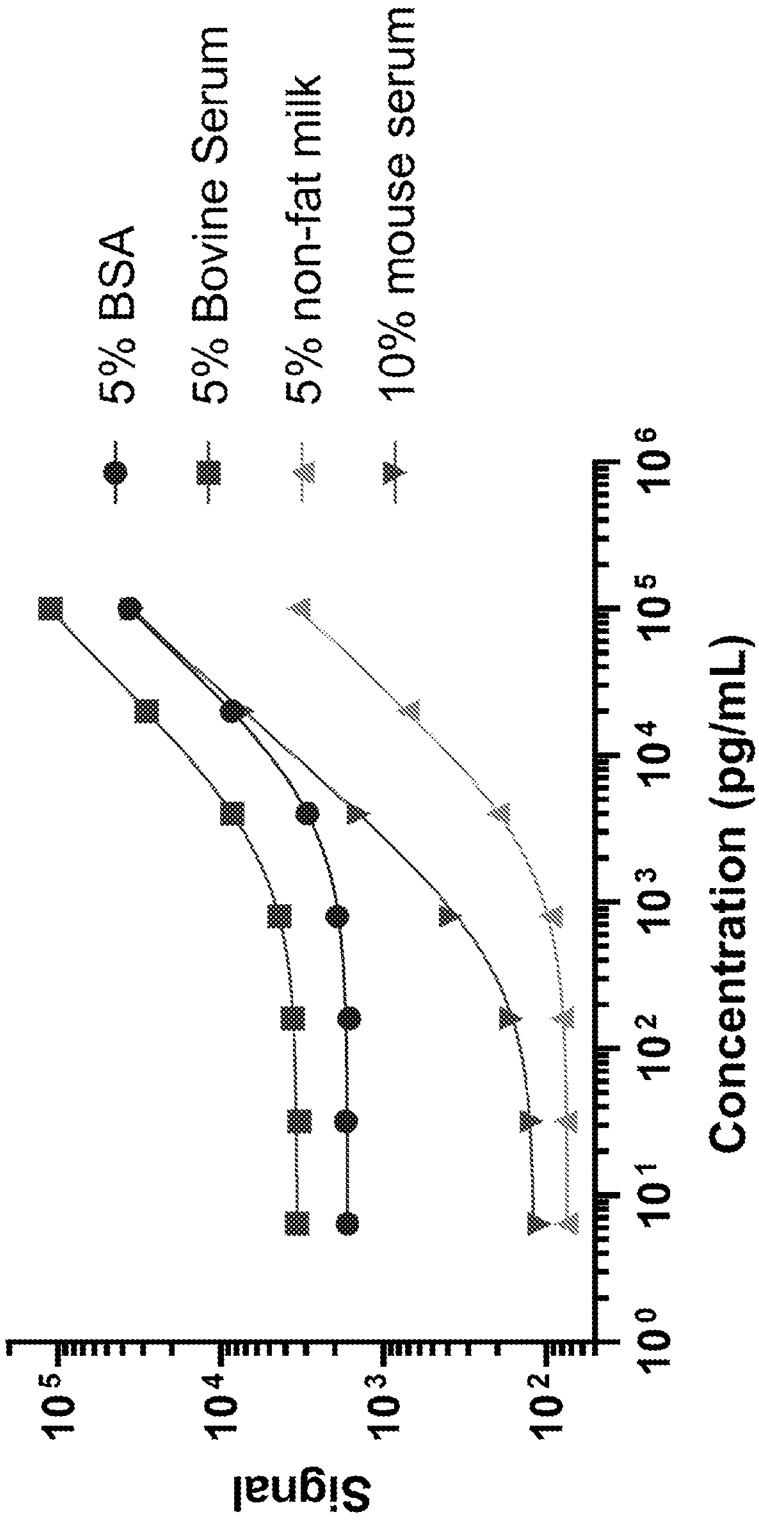
FIG. 3A is a graph comparing efficacy of various blocking buffers used in the detection assay.
Figure 3B:
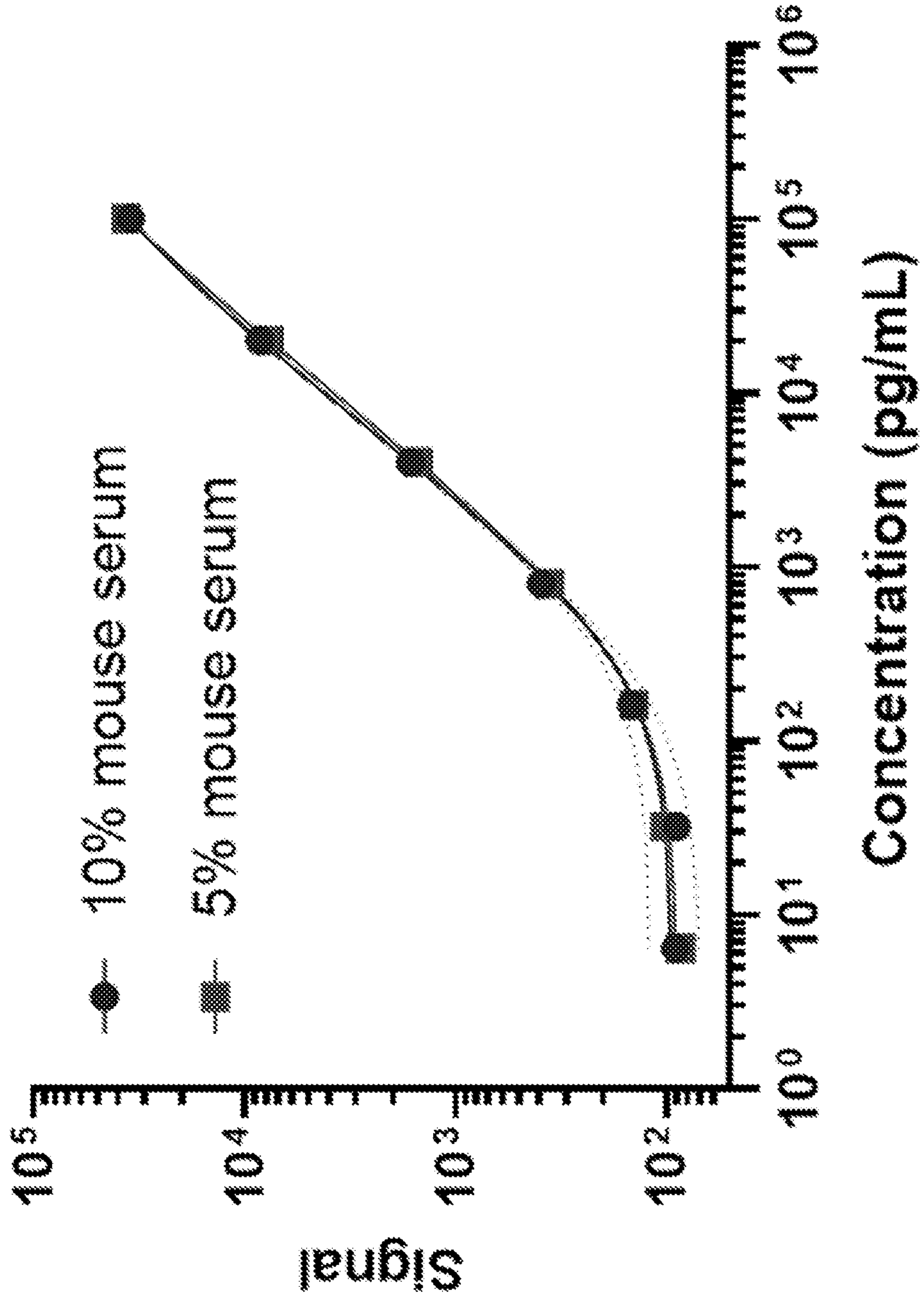
FIG. 3B is a graph comparing efficacy of blocking buffers comprising either 5% or 10% mouse serum for detecting a heteromeric protein complex.

To optimize the assay, blocking buffers of various compositions were tested. N-820 was used as a model for these experiments. As shown in FIG. 3A, the high background signal initially observed with 5% BSA blocking solution was improved by exchanging the blocking solution with a solution comprising 5% non-fat milk or 10% mouse serum. Assays using blocking solution that included 10% mouse serum blocking resulted in improved signal ranges and improved the lower limit of detection (LLOD) by approximately ten times. Blocking buffers with varying concentrations of mouse serum were then tested. Results illustrated in FIG. 3B show that buffers comprising either 5% or 10% mouse serum displayed similar blocking ability.

The concentrations of biotin-modified anti-IL15 capture antibody and SULFO-modified anti-IL15 detection antibody were optimized were then modified. The heteromeric N-820 protein complex was used as an exemplary model for these experiments. Results are shown in Table 1 and FIG. 4.

TABLE 1

Optimization of capture and detection antibody

| Biotin-αIL15 (μg/mL) | SULFO-αIL15 (μg/mL) | LLOD | Max signal | Signal/Noise |
|---|---|---|---|---|
| 0.0625 | 0.0625 | 72.7 | 30157 | 350 |
| 0.0625 | 0.125 | 82.6 | 26712 | 372 |
| 0.0625 | 0.25 | 112 | 33943 | 230 |
| 0.125* | 0.0626* | 69.5 | 33942 | 409 |
| 0.125 | 0.125 | 73.6 | 42655 | 374 |
| 0.125 | 0.25 | 54.8 | 35671 | 216 |

Matrix tolerance was tested using varying concentrations of serum, as listed in Table 2. The highest signal to noise ratio was observed using samples in 50% serum. The results indicated that the protein complex standards can be prepared in 50% serum, and patient samples for pharmacokinetic analysis can be diluted at least 2 times with assay diluent.

TABLE 2

Matrix tolerance test

| Matrix | PK LLOD (pg/mL) | Max signal | s/n |
|---|---|---|---|
| 100% | 83.2 | 35967 | 349 |
| 50%** | 57 | 42881 | 429 |
| 25% | 62.5 | 45593 | 368 |
| 12.50% | 72.6 | 48283 | 347 |
| 6.25% | 92.1 | 46314 | 286 |
| 3.13% | 81.2 | 48059 | 275 |

Example 2: Materials and Methods

Pharmacokinetic Assay Anti-IL-15 Antibody Bridging Experiment:

Two-hundred microliter solutions comprising 400 ng/mL of IL-15, N-820, or N-803 in 100% serum were prepared. A 1 in 4 serial dilution in 100% and 25% serum, respectively, was completed as follows:

For 100 ng/mL L-15, N-820, or N-803 solutions, 50 μL of 400 ng/mL IL-15, N-820, or N-803 was added to 150 μL serum. For 25 ng/mL solutions, 50 μL of 100 ng/mL IL-15, N-820, or N-803 was added to 150 μL serum. For 6.25 ng/mL solutions, 50 of 25 ng/mL of 400 ng/mL IL-15, N-820, or N-803 was added to 150 μL serum. For 1.563 ng/mL solution, 50 μL of 6.25 ng/mL IL-15, N-820, or N-803 was added to 150 serum. For 0.390 ng/mL solutions, 50 μL of 1.563 ng/mL IL-15, N-820, or N-803 was added to 150 μL serum. For 0.098 ng/mL solutions, 50 μL of 0.390 ng/mL IL-15, N-820, or N-803 was added to 150 μL serum. For 0 ng/mL, 150 μL of serum was used.

Solutions

The Blocking Solution was comprised of 5% (w/v) MSD Blocker A in PBS. For preparing the solution, 2.5 g of Blocker A was dissolved in 50 mL PBS. The solution was stored at 4° C. for up to 14 days. Before using, the Blocking solution was allowed to equilibrate to ambient temperature.

The Assay Diluent was comprised of 1% (w/v) Blocker A in PBS. The solution was prepared by adding 10 mL Blocking solution to 40 mL PBS. The solution was stored at 4° C., and was allowed to equilibrate to ambient temperature before use.

The Read Buffer was comprised of 10 mL 2× Read Buffer T diluted in 10 mL $H_2O$. The solution was mixed by inversion to avoid vortexing. The Read Buffer was stored at ambient temperature in a well-sealed bottle for a maximum of 30 days.

Biotinylated and SULFO-TAG Antibody Master Mix Preparation

Biotin and SULFO-TAG conjugated anti-IL15 antibodies were prepared in Assay Buffer at final concentrations of 1 μg/mL.

First, a 3.0 mL solution of 2.0 μg/mL Biotin-anti-IL15 (R&D Systems, MAB247), a 1.5 mL solution of 2.0 μg/mL SULFO-TAG conjugated anti-IL15 (Thermo) and a 1.5 mL solution of 2.0 μg/mL SULFO-TAG conjugated anti-IL15 (R&D Systems MAB247) in Assay Buffer were prepared. Subsequently, 1.5 mL of the 2.0 μg/mL of Biotin-anti-IL15 and 1.5 mL of the 2.0 μg/mL SULFO-TAG conjugated anti-IL15 were mixed to make a 3.0 mL solution.

Protocol

First, 100 μl Master Mix (comprising biotinylated and SULFO-TAG labeled antibody mixture) and 50 μl of either N-820 or N-803 was added to every other column of wells of a round-bottom 96-well polypropylene (PP) plate. The plate was sealed and incubated for 1-2 hours at room temperature with moderate shaking or overnight at 4° C.

During the Master Mix incubation, 150 μl of Blocking Buffer (5% Blocker A in PBS) was added per well to a Streptavidin GOLD (SA) plate. The plate was sealed and incubated at room temperature with shaking until sample incubation was completed (minimum 30 min). Blocking Buffer was then removed from the SA plate. The plate was washed with Wash Buffer once (150 μL/well). Fifty μl from each well of the PP plate was transferred to the SA plate. The SA plate was sealed and incubated with shaking at about 700 rpm for a minimum of 1 hour at room temperature. The plate was washed once with PBS-T (optional), and tapped dry. 150 μL of 2× Read Buffer T was added per well. The plate was then read. Results for this experiment are shown in FIG. 2.

Pharmacokinetic Assay Blocking Conditions Experiment:

Solutions

The Blocking Solution was comprised of either 5% (w/v) BSA in PBS, 5% non-fat milk in PBS, or 10% mouse serum in PBS.

Serum used in this experiment was Millipore SI-100ML (MP Bromedical #152282 lot #S1449).

The Assay Diluent was comprised of PBS or PBS-T, and each blocking solution was diluted 5× in PBS or PBS-T.

The Read Buffer was comprised of 10 mL 4× Read Buffer T+10 mL $H_2O$. Mixing was completed by inversion, and the solution was stored at ambient temperature in a well-sealed bottle for no longer than 30 days.

The stock concentration of biotin conjugated anti-IL-15 was 0.25 mg/mL (concentration was re-measured and confirmed by Bradford assay). The stock concentration of a new solution of SULFO-conjugated anti-IL-15 antibody (25× excess) was 0.30 mg/mL (concentration was re-measured confirmed by Bradford assay).

A 500 μL solution of 100 ng/mL N-820 100% serum was prepared.

A 1 in 4 serial dilution of the N-820 solution in 100% serum or assay diluent, respectively, was performed as follows: For a 20 ng/mL solution, 100 μL of 100 ng/mL N-820 was added to 400 μL serum or assay diluent. For a 4.0 ng/mL solution, 100 μL of 16.7 ng/mL N-820 was added to 400 μL serum or assay diluent. For a 0.8 ng/mL solution, 100 of 2.78 ng/mL N-820 was added to 400 μL serum or assay diluent. For a 0.16 ng/mL solution, 100 μL of 0.463 ng/mL N-820 was added to 400 μL serum or assay diluent. For a 0.032 ng/mL solution, 100 μL of 0.077 ng/mL N-820 was added to 400 μL serum or assay diluent. For a 0.0064 ng/mL solution, 100 μL of 0.013 ng/mL N-820 was added to 400 serum or assay diluent. For a 0 ng/mL solution, 400 μL of 100% serum was used.

Biotinylated and SULFO-TAG Antibody Master Mix Preparation

An equimolar ratio of biotinylated and SULFO-TAG anti-IL15 at a concentration of 0.125 μg/mL of each antibody was used for this experiment. The Biotin and SULFO-TAG conjugated anti-IL15 (new) were prepared in the Assay Buffer at the final concentrations of 0.125 μg/mL. A total of 7.4 mL of 0.125 μg/mL of Biotin and SULFO-TAG conjugated antibody was prepared.

Protocol:

One-hundred μl Master Mix (containing biotinylated and SULFO-TAG labeled antibody mixture) and 50 μl of N-820 solution was added to every other column of wells of a round-bottom 96-well polypropylene (PP) plate. The plate was sealed and incubated overnight at 4° C. with moderate shaking.

During the Master Mix incubation, 150 μl of Blocking Buffer (5% BSA in PBS) was added per well to a small spot Streptavidin (SSA) plate. The plate was sealed and incubated at room temperature with shaking until sample incubation was finished (minimum 30 min).

Blocking Buffer was removed from SSA plates, and the plates were tapped dry. From the PP plates, 50 μl from each well was transferred to the SSA plates. The SSA plates were sealed and incubated with shaking (700 rpm) for minimum of 1 hour at room temperature. The plates were washed 3× with PBS-T, and subsequently were tapped dry. One hundred fifty μL of 2× Read Buffer T was added to each well, and the plate was read.

In this experiment, the plate was not washed after blocking, and washing was done three times prior to adding Read-T buffer. Subsequent experiments include a single wash after blocking and a single wash prior to adding Read-T buffer.

Results for this experiments are shown in FIG. 3A, and illustrate that the LLOD was improved by ten times using 10% mouse serum.

Pharmacokinetic Assay Testing Various Concentrations of Antibody at an Equimolar Ratio:

Solutions

The Blocking Solution comprised 10% (v/v) Mouse Serum in PBS. The solution was prepared by diluting 1 mL mouse serum in 9 mL PBS. The solution was stored at 4° C. for a maximum of 14 days, and was allowed to equilibrate to ambient temperature before use.

The Assay Diluent was comprised of 2% (v/v) Mouse Serum in PBS. The solution was prepared by diluting 2 mL Blocking solution in 8 mL PBS. The Assay Diluent was stored at 4° C. and was allowed to equilibrate to ambient temperature before use.

The Read Buffer was used at a 2× concentration of Read Buffer T. Per plate, 10 mL of 4× Read Buffer T was diluted in 10 mL $H_2O$. The solution was mixed by inversion, and vortexing was avoided. The solution was stored at ambient temperature in a well-sealed bottle for a maximum of 30 days.

Normal serum was used at 100% and 10% concentrations. Serum was diluted in assay diluent.

The following protocol required 3.5 mL each of 100% and 10% serum.

A 500 µl solution of 100 ng/mL N-820 in either 100% or 10% serum was prepared, and was further diluted in a dilution series using 100% and 10% serum as diluent as follows.

A 1 in 5 serial dilution in 100% and 10% serum, respectively, was completed as follows: For a 20 ng/mL solution, 100 µL of 100 ng/mL N-820 was added to 400 µL serum. For a 4 ng/mL solution, 100 µL of 10 ng/mL N-820 was added to 400 serum. For a 0.8 ng/mL solution, 100 µL of 2.5 ng/mL N-820 was added to 400 serum. For a 0.16 ng/mL solution, 100 µL of 0.625 ng/mL N-820 was added to 400 µL serum. For a 0.032 ng/mL solution, 100 µL of 0.156 ng/mL N-820 was added to 400 serum. For a 0.0006 ng/mL solution, 100 µL of 0.039 ng/mL N-820 was added to 400 serum. For a 0 ng/mL solution, either 100% or 10% serum was used.

Biotinylated and SULFO-TAG Master Mix Preparation:

Equimolar ratios of biotinylated and SULFO-TAG antibodies were used for this experiment. A 2-fold serial dilution was prepared of the Biotin and SULFO-TAG conjugated anti-IL15 in the Assay Buffer with final concentrations of 0.5, 0.25, and 0.125 µg/mL.

A 1.0 µg/mL solution of Biotin and SULFO-TAG conjugated antibody in Assay Buffer was prepared. The protocol required 1.8 mL each of 1.0 µg/mL of Biotin and SULFO-TAG conjugated antibody in Assay Buffer.

The antibody solution was prepared by mixing 1.8 mL each of 1.0 µg/mL of Biotin and SULFO-TAG conjugated antibody. The resultant solution had 0.5 µg/mL of Biotin and SULFO-TAG conjugated antibody (final concentration).

From the above solution 1.5 mL was taken and diluted with 1.5 mL of Assay diluent to make a 0.25 µg/mL solution. From the 0.25 µg/mL solution 1.0 mL was taken and diluted with 1.0 mL of assay diluent to make a 0.125 µg/mL solution.

Results indicate that the heteromeric protein complex is detectable in 100% serum samples using equimolar concentrations of capture and detection antibody.

Pharmacokinetic Assay Testing Various Antibody Ratios:

Solutions

The Blocking Solution comprised 5% (v/v) Mouse Serum in PBS. The solution was prepared by diluting 1 mL mouse serum in 19 mL PBS. The solution was stored at 4° C. for up to 14 days and allowed to equilibrate to ambient temperature before use.

The Assay Diluent was comprised of 1% (v/v) Mouse Serum in PBS, 2 mL Blocking solution, and 8 mL PBS. The solution was stored at 4° C. and equilibrated to ambient temperature before use.

The Read Buffer was comprised of 2× Read Buffer T. For each plate, 10 mL 4× Read Buffer T was added to 10 mL $H_2O$. The solution was mixed by inversion, and vortexing was avoided. The solution was stored at RT in a sealed bottle for a maximum of 30 days.

Normal serum was diluted to 25% for a total volume of 1.4 mL, and 1.4 mL of 10 ng/mL N-820 in 25% serum was prepared.

Biotinylated and SULFO-TAG Antibody Master Mix Preparation

Two-fold serial dilutions of the Biotin and SULFO-TAG conjugated antibody in the Assay Buffer were prepared separately.

Two µg/mL of Biotin conjugated antibody and 4.0 µg/mL SULFO-TAG conjugated antibody were prepared. The study required 1.0 mL each of 2.0 µg/mL of Biotin and 4.0 µg/mL of SULFO-TAG conjugated antibody in Assay Buffer.

A 2-fold serial dilution for Biotin conjugated antibody was completed as follows: For a 1.0 µg/mL solution, 0.5 mL of 2.0 µg/mL solution (above) was added to 0.5 mL of assay buffer. For a 0.5 µg/mL solution, 0.5 mL of 1.0 µg/mL solution was added to 0.5 mL of assay buffer. For a 0.25 µg/mL solution, 0.5 mL of 0.5 µg/mL solution was added to 0.5 mL of assay buffer. For a 0.125 µg/mL solution, 0.5 mL of 0.25 µg/mL solution was added to 0.5 mL of assay buffer. Assay buffer only was used for 0 µg/mL.

Two-fold serial dilution for SULFO-TAG conjugated antibody was completed as follows: For 4.0 µg/mL, 1.0 mL of the above solution was used. For a 2.0 µg/mL solution, 0.5 mL of 4.0 µg/ml solution (above) was added to 0.5 mL of assay buffer. For 1.0 µg/mL solution, 0.5 mL of 2.0 µg/mL solution was added to 0.5 mL of assay buffer. For 0.5 µg/mL solution, 0.5 mL of 1.0 µg/mL solution was added to 0.5 mL of assay buffer. For 0.25 µg/mL solution, 0.5 mL of 0.5 µg/mL solution was added to 0.5 mL of assay buffer. For 0.125 µg/mL solution, 0.5 mL of 0.25 µg/mL solution was added to 0.5 mL of assay buffer. Assay buffer only was used for 0 µg/mL.

Protocol

To each well of a flat-bottom 96-well polypropylene plate, 25 µl of biotinylated antibody and 25 µl of SULFO-TAG labeled antibody (total 50 µl/well of Master Mix) and 25 µl of N-820 were added. The plate was sealed and incubated with moderate shaking (500 rpm) overnight at 4° C.

During the Master Mix incubation, 150 µl per well of Blocking Buffer (5% Mouse Serum in PBS) was added to a Small-spot Streptavidin GOLD (SSA) plate. The plate was sealed and incubate at room temperature with shaking until sample incubation was finished (minimum 30 min).

The Blocking Buffer was removed from SA plate. The plate was washed with Wash Buffer once (150 µL/well). From each well of the PP plate 50 µl of solution was transferred to the SSA plate. The SSA plate was sealed and incubated with shaking (700 rpm) for a minimum 1 hour at room temperature. The plate was washed once with PBS-T and tapped dry. Per well, 150 µl of 2× Read Buffer T was added and the plate was read. Results are shown in Table 3.

TABLE 3

Results for testing various ratios of capture and detection antibody

| | | Biotin (µg/ml) | | | | | |
|---|---|---|---|---|---|---|---|
| SULFO (µg/ml) | | 1<br>1 | 0.5<br>2 | 0.25<br>3 | 0.125<br>4 | 0.0625<br>5 | 0<br>6 |
| 2 | A | 7839 | 7513 | 4794 | 2900 | 1563 | 89 |
| 1.16 | B | 6957 | 7468 | 6007 | 3666 | 1949 | 76 |
| 0.676 | C | 5882 | 7342 | 6647 | 4402 | 2608 | 60 |
| 0.393 | D | 4581 | 6632 | 6849 | 5595 | 3697 | 65 |
| 0.229 | E | 3257 | 5716 | 6890 | 6303 | 4901 | 62 |
| 0.133 | F | 2099 | 4243 | 5893 | 6064 | 4719 | 58 |
| 0.077 | G | 1297 | 3069 | 4327 | 5934 | 4934 | 62 |
| 0 | H | 68 | 59 | 61 | 64 | 64 | 61 |
| | | Biotin (µg/ml) | | | | | |
| SULFO (µg/ml) | | 1<br>7 | 0.5<br>8 | 0.25<br>9 | 0.125<br>10 | 0.0625<br>11 | 0<br>12 |
| 2 | A | 2641 | 2165 | 1139 | 637 | 440 | 95 |
| 1.16 | B | 1488 | 1159 | 653 | 438 | 245 | 80 |
| 0.676 | C | 909 | 635 | 377 | 238 | 165 | 78 |
| 0.393 | D | 503 | 379 | 256 | 186 | 139 | 68 |
| 0.229 | E | 313 | 267 | 207 | 124 | 98 | 70 |

TABLE 3-continued

Results for testing various ratios of capture and detection antibody

| | | | | | | | |
|---|---|---|---|---|---|---|---|
| 0.133 | F | 220 | 162 | 127 | 102 | 82 | 63 |
| 0.077 | G | 146 | 119 | 99 | 78 | 75 | 67 |
| 0 | H | 66 | 60 | 71 | 61 | 63 | 58 |

Pharmacokinetic Assay Testing Mouse Serum Blocking Solution:

The effect of 10% and 5% mouse serum from two different vendors (Sigma vs MP Biomedicals) was compared in the below study.

Solutions

The Blocking Solution comprised of either 10% (v/v) Mouse Serum or 5% (v/v) Mouse Serum in PBS. The solutions were made by diluting 1 mL mouse serum in 9 mL PBS, and were stored at 4° C. for a maximum of 4 days. The solutions were allowed to equilibrate to ambient temperature before use.

The Assay Diluent was comprised of 2% (v/v) Mouse Serum in PBS. The Assay Diluent was prepared by adding 2 mL Blocking solution to 8 mL PBS. The solution was stored at 4° C., was allowed to equilibrate to ambient temperature before use.

The Read Buffer was comprised of 2× Read Buffer T. For each plate, 10 mL of 4× Read Buffer T was mixed with 10 mL $H_2O$. The buffer was mixed by inversion, and vortexing was avoided. The solution was stored at ambient temperature in a well-sealed bottle for up to 30 days.

N-820 Sample Preparation

N-820 was prepared at a concentration of 100 ng/mL at a volume of 500 μL. N-820 samples were prepared in 100% and 10% serum.

One in five serial dilution in 100% and 10% serum were prepared as follows: For 20 ng/mL N-820, 100 μL of 100 ng/mL was added to 400 μL serum. For 4 ng/mL N-820, 100 μL of 10 ng/mL was added to 400 μL serum. For 0.8 ng/mL N-820, 100 μL of 2.5 ng/mL was added to 400 μL serum. For 0.16 ng/mL N-820, 100 μL of 0.625 ng/mL was added to 400 μL serum. For 0.032 ng/mL N-820, 100 μL of 0.156 ng/mL was added to 400 serum. For 0.006 ng/mL N-820, 100 μL of 0.039 ng/mL was added to 400 μL serum. For 0 ng/mL N-820, 100 uL diluent was added to 400 μL of 100% or 10% serum.

Biotinylated and SULFO-TAG Antibody Master Mix Preparation 2 mL of 0.125 μg/mL biotin- and SULFO-anti-IL15 was prepared in either 2% MS in PBS, 1% MS (Sigma) in PBS, and 1% MS (MB bioscience) in PBS.

Protocol

100 μl Master Mix (containing biotinylated and SULFO-TAG labeled antibody mixture) and 50 μl of N-820 solution was added to every other column of a flat-bottom 96-well polypropylene plate. The plate was sealed and incubated with moderate shaking (500 rpm) overnight at 4° C. The next day, 150 μl per well of Blocking Buffer (10% Mouse Serum in PBS) was added to a Small Spot Streptavidin GOLD (SSA) plate. The plate was sealed and incubated at room temperature with shaking for at minimum 30 min.

The Blocking Buffer was removed from the SSA plate. The plate was washed with Wash Buffer once (150 μL/well). From each well of the PP plate 50 μl was transferred to the SSA plate. The SSA plate was sealed and incubated with shaking (700 rpm) for minimum 1 hour at room temperature.

The Blocking Buffer was removed from SSA plate. The plate was washed with Wash Buffer once (150 μL/well). Then, 50 μl from each well of the PP plate was transferred to the SSA plate. The SSA plate was sealed and incubated with shaking (700 rpm) for minimum 1 hour at room temperature. The source of mouse serum did not affect assay results.

Pharmacokinetic Assay Optimizing Antibody Ratios:

Solutions

The Blocking Solution comprised 5% (v/v) Mouse Serum in PBS. The solution was prepared by adding 1 mL mouse serum to 9 mL PBS. The solution was stored at 4° C. for a maximum of 14 days, and was allowed to equilibrate to ambient temperature before use.

The Assay Diluent comprised 1% (v/v) Mouse Serum in PBS. The solution was prepared by adding 2 mL Blocking solution to 8 mL PBS. The solution was stored at 4° C., and was allowed to equilibrate to ambient temperature before use.

The Read Buffer was comprised of 2× Read Buffer T. For each plate, 10 mL of 4× Read Buffer T was added to 10 mL $H_2O$. The solution was mixed by inversion, and vortexing was avoided. The solution was stored at ambient temperature in a sealed bottle for a maximum of 30 days.

N-820 Sample Preparation:

600 μL of 100 ng/mL N-820 was first prepared in 100% serum.

One in four serial dilutions in 100% serum was prepared as follows: For a 25 ng/mL solution, 150 μL of 100 ng/mL N-820 was added to 450 μL serum. For a 6.25 ng/mL solution, 150 μL of 25 ng/mL N-820 was added to 450 μL serum. For a 1.563 ng/mL solution, 150 μL of 6.25 ng/mL N-820 was added to 450 μL serum. For a 0.391 ng/mL solution, 150 μL of 1.563 ng/mL N-820 was added to 450 μL serum. For a 0.098 ng/mL solution, 150 μL of 0.391 ng/mL N-820 was added to 450 μL serum. For a 0.024 ng/mL solution, 150 μL of 0.098 ng/mL N-820 was added to 450 μL serum. For 0 ng/mL, 100% serum was used.

Biotinylated and SULFO-TAG Antibody Master Mix Preparation

A 2-fold serial dilution for each antibody (biotin conjugated antibody) at a volume of 1.5 mL for each concentration was prepared.

First, 2.3 mL of 0.25 μg/mL antibody was prepared. For 0.125 μg/mL solution, 0.75 mL of 0.25 μg/mL solution was added to 0.75 mL of assay buffer.

A 2-fold serial dilution for each antibody (SULFO-TAG conjugated antibody) at a volume of 1 mL for each concentration was prepared.

First 2.0 mL of 0.5 μg/mL antibody was prepared. For 0.25 μg/mL, 0.8 mL of 0.5 μg/mL solution was mixed with 0.8 mL of assay buffer. For 0.125 μg/mL, 0.5 mL of 0.25 μg/mL solution was mixed with 0.5 mL of assay buffer.

To every other column of a flat-bottom 96-well polypropylene plate 50 μl of biotinylated antibody and 50 μl of SULFO-TAG labeled antibody (total 100 μl/well of Master Mix) and 50 μl of N-820 solution was added. The plate was sealed and incubated with moderate shaking (500 rpm) overnight at 4° C. The next day, 150 μl of Blocking Buffer (5% Mouse Serum in PBS) was added to each well of a Small Spot Streptavidin GOLD (SSA) plate. The plate was sealed and incubated at room temperature with shaking for at minimum 30 min. The Blocking Buffer was removed from the SSA plate. The plate was washed once with Wash Buffer (150 μL/well). Subsequently, 50 μl was transferred from each well of the PP plate to the SSA plate. The SSA plate was sealed and incubated with shaking (700 rpm) for minimum 1 hour at room temperature. The plate was washed once with PBS-T, and was tapped dry. Per well, 150 μL of 2× Read Buffer T was added, and the plate was read.

Figure 4:
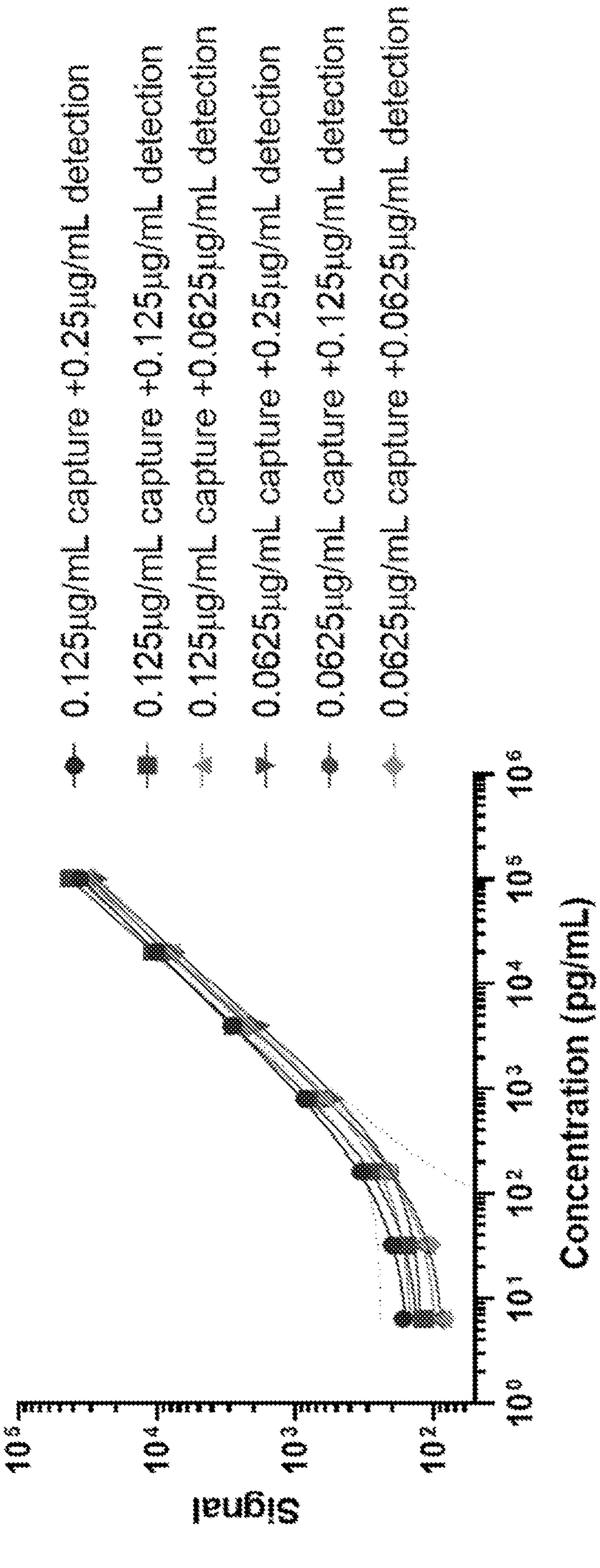
FIG. 4 is a graph showing detection of the protein complex using different concentrations of capture and detection antibody.

Results are illustrated in FIG. 4.

Pharmacokinetic Assay Matrix Tolerance Experiment: Solutions

The Blocking Solution comprised 5% (v/v) Mouse Serum in PBS. The solution was prepared by adding 1 mL mouse serum to 9 mL PBS. The solution was stored at 4° C. for a maximum of 14 days, and was allowed to equilibrate to ambient temperature before use.

The Assay Diluent comprised 1% (v/v) Mouse Serum in PBS. The solution was prepared by mixing 2 mL Blocking solution and 8 mL PBS. The solution was stored at 4° C., and allowed to equilibrate to ambient temperature before use.

The Read Buffer was comprised of 2× Read Buffer T. For each plate, 10 mL 4× Read Buffer T was added to 10 mL $H_2O$. The solution was mixed by inversion, and vortexing was avoided. The solution was stored at ambient temperature in a sealed bottle for a maximum of 30 days N-820 Sample Preparation Solutions were prepared as follows: For 100% serum, 4 mL of 100% serum was used. For 0% serum, 2 mL of 100% serum (above) was added to 2 mL of assay diluent. For 25% serum, 2 mL of 50% serum was added to 2 mL of assay diluent. For 12.5% serum, 2 mL of 25% serum was added to 2 mL of assay diluent. For 6.25% serum, 2 mL of 12.5% serum was added to 2 mL of assay diluent. For 3.12% serum, 2 mL of 6.25% serum +2 mL of assay diluent.

Next, 2 mL of 100 ng/mL of N-820 in 100% serum was prepared, and 5.5 mL of 100 ng/mL of N-820 in assay diluent was prepared.

Mixtures were prepared as follows: For 100% serum (100 ng/mL N-820) sample, 2 mL of 100 ng/mL N-820 in was prepared in 100% serum. For 50% serum (100 ng/mL N-820) sample, 1 mL of 100 ng/mL N-820 in 100% serum was added to 1 mL of 100 ng/mL N-820 in assay diluent. For 25% serum (100 ng/mL N-820) sample, 1 mL of 100 ng/mL N-820 in 50% serum was added to 1 mL of 100 ng/mL N-820 in assay diluent. For 12.5% serum (100 ng/mL N-820) sample, 1 mL of 100 ng/mL N-820 in 25% serum was added to 1 mL of 100 ng/mL N-820 in assay diluent. For 6.25% serum (100 ng/mL N-820) sample, 1 mL of 100 ng/mL N-820 in 12.5% serum was added to 1 mL of 100 ng/mL N-820 in assay diluent. For 3.12% serum (100 ng/mL N-820) sample, 1 mL of 100 ng/mL N-820 in 6.25% serum was added to 1 mL of 10 Ong/mL N-820 in assay diluent.

For testing 100% serum, samples were prepared by subjecting the above samples to 4-fold serial dilutions in 100% serum.

For 100 ng/mL N-820, 0.5 mL of 100% serum (100 ng/mL N-820) was used. For 20 ng/mL N-820, 0.05 mL of 100 ng/mL N-820 and 0.15 mL of 100% serum were mixed. For 4 ng/mL N-820, 0.05 mL of 20 ng/mL solution and 0.15 mL of 100% serum were mixed. For 0.8 ng/mL N-820, 0.05 mL of 4 ng/mL solution and 0.15 mL of 100% serum were mixed. For 0.16 ng/mL N-820, 0.05 mL of 0.8 ng/mL solution and 0.15 mL of 100% serum were mixed. For 0.032 ng/mL N-820, 0.05 mL of 0.16 ng/mL N-820 solution and 0.15 mL of 100% serum were mixed. For 0.006 ng/mL N-820, 0.05 mL of 0.032 ng/mL solution and 0.15 mL of 100% serum were mixed. For 0 μg/mL N-820, 0.15 mL 100% serum was used.

For testing 50% serum, the samples were prepared by subjecting the above samples to 4-fold serial dilutions in 50% serum.

For 100 ng/mL N-820, 1.0 mL of 50% serum (100 ng/mL N-820) was used. For 20 ng/mL N-820, 0.05 mL of 100 ng/mL N-820 and 0.15 mL of 50% serum were mixed. For 4 ng/mL N-820, 0.05 mL of 20 ng/mL solution and 0.15 mL of 50% serum were mixed. For 0.8 ng/mL N-820, 0.05 ml of 4 ng/mL solution and 0.15 mL of 50% serum were mixed. For 0.16 ng/mL N-820, 0.05 mL of 0.8 ng/mL solution and 0.15 mL of 50% serum were mixed. For 0.032 ng/mL N-820, 0.05 mL of 0.16 ng/mL solution and 0.15 mL of 50% serum were mixed. For 0.006 ng/mL N-820, 0.05 mL of 0.032 ng/ml solution and 0.15 ml of 50% serum were mixed. For 0 μg/mL N-820, 0.15 mL of 50% serum was used.

Dilutions were repeated as appropriate for 25%, 12.5%, 6.25% and 3.12% serum samples.

Biotinylated and SULFO-TAG Antibody Master Mix Preparation

Biotin-anti-IL15 and SULFO-anti-IL15 at concentrations of 0.125 ug/mL were prepared in assay diluent at a final volumes of 5.5 ml. The solutions were combined and mixed well.

Protocol

To every other well of a flat-bottom 96-well polypropylene plate, 100 μl of Master Mix (containing biotinylated and SULFO-TAG labeled antibody mixture) and 50 μl of N-820 solution were added. The plate was sealed and incubated with moderate shaking (500 rpm) overnight at 4° C.

During the Master Mix incubation, 150 μl was added per well of Blocking Buffer (5% Mouse Serum in PBS) to a Small-Spot Streptavidin GOLD (SSA) plate. The plate was sealed and incubated at room temperature with shaking until sample incubation was finished (minimum 30 min).

Blocking Buffer was removed from the SSA plate. The plate was washed with 150 μL per well of Wash Buffer once. From the PP plate, 50 μl from each well was transferred to the SSA plate. The SSA plate was sealed and incubated with shaking (700 rpm) at room temperature for 2 hours. The plate was washed once with PBS-T, and was tapped dry. To each well, 150 μL of 2× Read Buffer T was added and the plate was read.

Figure 5:
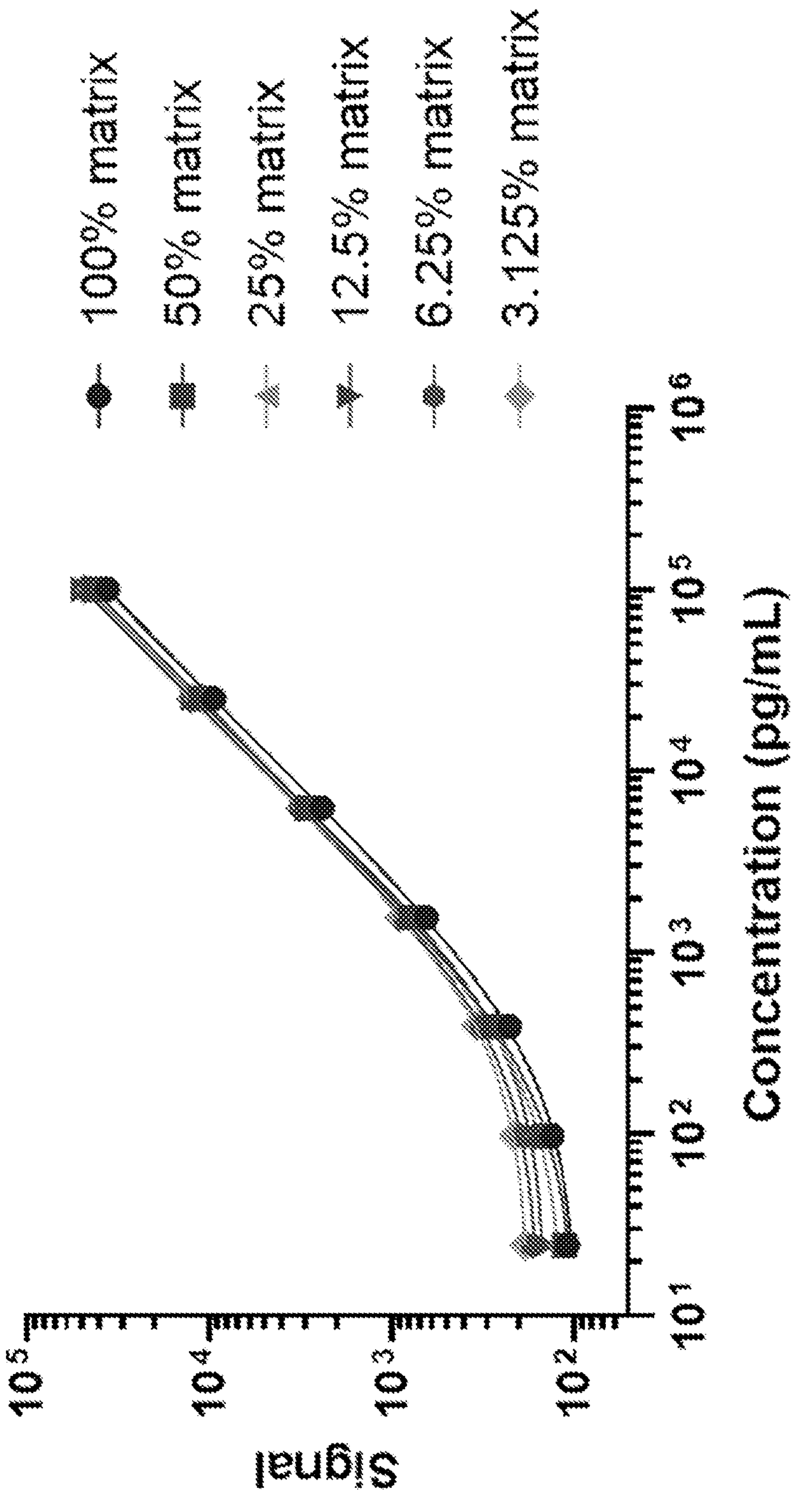
FIG. 5 is a graph illustrating matrix tolerance of the assay.

Results are shown in FIG. 5, and illustrate that standards can be prepared in 50% serum and patient samples can be diluted at least 2 times.

What is claimed is:

1. A composition comprising:

(i) an interleukin-15 (IL-15)/interleukin-15 receptor alpha Sushi domain (IL-15RαSu) complex comprising:

a) a first IL-15RαSu domain comprising SEQ ID NO:1;

b) a second IL-15RαSu domain comprising SEQ ID NO:1, wherein the first and second IL-15RαSu domains are directly or indirectly joined by a disulfide bond;

c) a first IL-15 domain, bound by electrostatic interactions to the first IL-15RαSu domain to form a first IL-15/IL-15RαSu complex;

d) a second IL-15 domain, bound by electrostatic interactions to the second IL-15RαSu domain to form a second IL-15/IL-15RαSu complex;

(ii) a first anti-IL-15 monoclonal antibody (mAb) bound to an epitope on the first IL-15/IL-15RαSu complex, wherein the first anti-IL-15 monoclonal antibody is biotinylated for conjugation to a streptavidin-conjugated polymeric surface; and (iii) a second anti-IL-15 mAb bound to the second IL-15/IL-15RαSu complex, wherein the anti-IL-15 second mAb comprises a detection means selected from the group consisting of a fluorophore, a radioisotope, and an enzyme;

wherein both the first anti-IL-15 mAb and the second anti-IL-15 mAb comprise the same epitope binding domain.

2. The composition of claim 1, wherein the IL-15RαSu domains each further comprise an immunoglobulin crystalizable fragment (Fc) domain.

3. The composition of claim 2, wherein the IL-15 domains further comprise a single chain variable fragment (scFv) domain.

4. The composition of claim 2, wherein the IL-15RαSu domains further comprise an scFv domain.

5. The composition of claim 1, wherein the first and second IL-15RαSu domains are directly joined by a disulfide bond.

6. The composition of claim 2, wherein the first and second IL-15RαSu domains are indirectly joined by a disulfide bond between the Fc domains.

7. The method of claim 1, wherein both the first IL-15 mAB and the second IL-15 mAb each comprise anti-IL-15 mAb MAB247.

8. A method for detecting a heterotetrameric IL-15/IL-15RαSu complex in a biological sample, the method comprising:

a) contacting the biological sample comprising the IL-15/IL-15RαSu complex with a first anti-IL-15 mAb, wherein the anti-IL-15 mAb is biotinylated for conjugation to a streptavidin-conjugated polymeric surface, wherein the IL-15/IL-15RαSu complex comprises two IL-15 domains and two IL-15RαSu domains each comprising SEQ ID NO:1, wherein each IL-15 domain is electrostatically bound to an IL-15RαSu domain, wherein the two IL-15RαSu domains are directly or indirectly bound to each other by a disulfide bond, and wherein the Fab portion of the anti-IL-15 mAb binds an epitope on the IL-15/IL-15RαSu complex with an affinity between 500 nM and 1 fM;

b) contacting the biological sample with a second anti-IL-15 mAb under conditions such that the second anti-IL-15 antibody binds to the identical epitope on the second IL-15/IL-15RαSu complex, wherein the second anti-IL-15 mAb comprises a detection means selected from the group consisting of a fluorophore, a radioisotope, and an enzyme;

c) washing unbound complexes from the polymeric surface; and d) detecting binding of the second anti-IL-15 mAb.

9. The method of claim 8, wherein the IL-15RαSu domains each further comprise an Fc domain.

10. The method of claim 9, wherein the polymeric surface is a polypropylene or polystyrene surface.

11. The method of claim 9, wherein the IL-15 domains each further comprise an scFv domain.

12. The method of claim 8, wherein the first and second IL-15RαSu domains are directly joined by a disulfide bond.

13. The method of claim 9, wherein the first and second IL-15RαSu domains are indirectly joined by a disulfide bond between the Fc domains.

14. The method of claim 8, wherein both the first IL-15 mAB and the second IL-15 mAb each comprise anti-IL-15 mAb MAB247.

* * * * *